United States Patent
Bartorelli Cusani (10) Patent No.: US 11,352,398 B2
(45) Date of Patent: Jun. 7, 2022

(54) RECOMBINANT PROTEIN UK 114 IN STABLE POLYMER FORM FOR USE IN THE TREATMENT, DIAGNOSIS AND PREVENTION OF MALIGNANT SOLID AND SYSTEMIC TUMOURS

(71) Applicant: Alberto Bartorelli Cusani, Monte Carlo (MC)

(72) Inventor: Alberto Bartorelli Cusani, Monte Carlo (MC)

(*) Notice: Subject to any disclaimer, the term of this patent is extended or adjusted under 35 U.S.C. 154(b) by 188 days.

(21) Appl. No.: 16/468,921

(22) PCT Filed: Dec. 14, 2017

(86) PCT No.: PCT/EP2017/082849
§ 371 (c)(1),
(2) Date: Jun. 12, 2019

(87) PCT Pub. No.: WO2018/109096
PCT Pub. Date: Jun. 21, 2018

(65) Prior Publication Data
US 2020/0017559 A1 Jan. 16, 2020

(30) Foreign Application Priority Data
Dec. 16, 2016 (IT) .......................... 102016000127428

(51) Int. Cl.
*C07K 14/47* (2006.01)
*A61K 38/00* (2006.01)
*A61P 35/00* (2006.01)
*A61K 39/00* (2006.01)

(52) U.S. Cl.
CPC .......... *C07K 14/47* (2013.01); *A61K 39/0011* (2013.01); *A61P 35/00* (2018.01); *A61K 38/00* (2013.01); *A61K 2039/572* (2013.01)

(58) Field of Classification Search
None
See application file for complete search history.

(56) References Cited

U.S. PATENT DOCUMENTS 5,595,756 A * 1/1997 Bally .................. A61K 9/1272
264/4.1

FOREIGN PATENT DOCUMENTS

| WO | 1999043340 A1 | 9/1999 |
| WO | 2000063368 A1 | 10/2000 |
| WO | 2004076614 A2 | 9/2004 |

OTHER PUBLICATIONS

Zugazagoitia et al, Current Challenges in Cancer Treatment, Clinical Therapies, vol. 38, (2016), pp. 1551-1566 (Year: 2016).*
Sporn et at, "Chemoprevention of Cancer," Carcinogenesis, vol. 21 (2000), 525-530 (Year: 2000).*
Bussolati G. et al., "Cytolytic and tumor inhibitory antibodies against UK114 protein in the sera of cancer patients", International Journal of Oncology, vol. 10, No. 4, Apr. 1, 1997 pp. 779-785.
Ceciliani F. et al., "The primary structure of UK114 tumor antigen", FEBS Letters, Elsevier, Amsterdam, NL, vol. 393, Sep. 16, 1996, pp. 147-150.
Funaro A. et al., "Identification of a 220-kDa membrane tumor-associated antigen by human anti-UK114 monoclonal antibodies selected from the immunoglobulin repertoire of a cancer patient", Experimental Cell Research, Elsevier, Amsterdam, NL, vol. 247, No. 2, Mar. 15, 1999, pp. 441-450.
Search Report and Written Opinion of PCT/EP2017/082849 of Apr. 3, 2018.

* cited by examiner

*Primary Examiner* — Thomas S Heard
(74) *Attorney, Agent, or Firm* — Silvia Salvadori, P.C.; Silvia Salvadori (57) ABSTRACT

Disclosed is a novel recombinant protein UK 114 in stable polymer form for use in the treatment, diagnosis and prevention of malignant solid and systemic tumours.

4 Claims, 8 Drawing Sheets

Specification includes a Sequence Listing.

Cytometric assay for viability and cell death (Propidium Iodide + Annexin V) on cell line RPMI 8226 (Human Multiple Myeloma)

Anti native UK114

M1 necrotic cells,
M2 late apoptotic cells,
M3 live cells,
M4 early apoptotic cells

Figure 9a

Cytometric assay for viability and cell death (Propidium Iodide + Annexin V) on cell line RPMI 8226 (Human Multiple Myeloma)

Anti native UK101

M1 necrotic cells,
M2 late apoptotic cells,
M3 live cells,
M4 early apoptotic cells

Figure 9b

Cytometric assay for viability and cell death (Propidium Iodide + Annexin V) on cell line RPMI 8226 (Human Multiple Myeloma)

M1 necrotic cells,
M2 late apoptotic cells,
M3 live cells,
M4 early apoptotic cells Negative control

Figure 9c

Cytometric assay for viability and cell death (Propidium Iodide + Annexin V) on cell line RPMI 8226 (Human Multiple Myeloma)

M1 necrotic cells,
M2 late apoptotic cells,
M3 live cells,
M4 early apoptotic cells Anti PRP14

RECOMBINANT PROTEIN UK 114 IN STABLE POLYMER FORM FOR USE IN THE TREATMENT, DIAGNOSIS AND PREVENTION OF MALIGNANT SOLID AND SYSTEMIC TUMOURS

This application is a U.S. national stage of PCT/EP2017/082849 filed on 14 Dec. 2017, which claims priority to and the benefit of Italian Application No. 102016000127428 filed on 16 Dec. 2016, the contents of which are incorporated herein by reference in their entireties.

The present invention relates to recombinant YjgF/YER057c/UK114 RID proteins (YjgF/YER057c/UK114) in stable polymer form for use in the treatment, diagnosis and prevention of malignant solid and systemic tumours.

PRIOR ART

The family of proteins called YjgF/YER057c/UK114, which are highly conserved in various prokaryotic and eukaryotic organisms, has formed the subject of numerous studies designed to investigate the structural and functional characteristics of said proteins (Bartorelli et al., J. Tumor and Marker Oncology, 1994, 9, 37; Lambrecht J A et al., J. Biol. Chem., 2010, 285, 34401-34407; Lambrecht J A et al., J. Biol. Chem. 2012, 287, 3454-3461; Mistiniene E et al., Bioconjugate Chem. 2003, 14, 1243-1252; Dhawan L et al., Mol. Cell. Biol., 2012, 32, 3768-3775; Flynn J M et al., Mol. Microbiol., 2013, 89(4)751-759; Ernst D C et al., J. Bacteriology, 2014, 196 (18), 3335-3342; Niehaus T D et al., BMC Genomics, 2015, 16, 382). UK114 belongs to the YjgF/YER057c/UK 114 family. The common denominator of members of said family is their biological activity, especially the deaminase activity of 2-amino-acrylate (see Lambrect et al., 2012). Said activity defines all members of the YjgF/YER057c/UK 114 family with the acronym RID.

WO 9602567 describes the antitumoral activity of a perchloric acid soluble goat liver extract (called UK 101) containing protein UK 114. Said protein has a molecular weight of 14.2 kDa and the sequence of 137 amino acids as reported in Ceciliani F. et al., FEBS Letters, 1996, 393, 147-150.

The native protein UK 114, isolated from various species and/or proteins cross-reacting with it, is only present in the cytoplasm of normal cells, whereas various percentages thereof are also present in the cell membrane of malignant solid systemic tumour cells (Bartorelli A, et al., Int J Oncol. 1996 March; 8(3):543-8.; Bussolati G, et al., Int J Oncol. 1997 April; 10(4):779-85). In adenocarcinomas, it is expressed in over 80% of tumours. E. coli expression of protein UK 114 in recombinant form was described in WO 0063368 and in Colombo I et al. (Biochim. Biophys. Acta, 1998, 1442, 49-59) and Burman J D et al., (BMC Structural Biology, 2007, 7, 30), but, unlike WO 0063368, which reported a dimeric structure, Deriu D et al., (Acta Cryst., 2003, D59, 1676-1678), reported that protein UK 114 in crystalline form has a trimeric configuration. It is known from the literature that protein UK114 with a monomeric structure (Oka et al., 1995 J. Biol. Chem. 270:30060-30067) can present in an unstable dimeric or trimeric form. Experimentally, various physicochemical conditions, especially various ion and protein denaturation concentrations, can cause the dimeric or trimeric protein UK114 to take on a monomeric conformation, as demonstrated by chromatographic and mass spectrometry analysis. According to studies by Mistiniene et al., recombinant protein UK114 (obtained from E. coli) appears in monomeric form under conditions of slight denaturation induced by KCl 3M or 3M guanidine hydrochloride, whereas in 0.1M NaCl solution, it is in trimeric form. This variability of results is due to the tendency of the trimer to dissociate into a monomer under various conditions of instability.

In any event, no immunogenic activity of the form considered trimeric has been described, while studies conducted by the Applicant demonstrate that the recombinant protein obtained from monomeric E. coli does not produce any antibody response when injected into xenogeneic mammals. The recombinant proteins disclosed in Colombo I. et al., (Biochim. Biophys. Acta, 1998, 1442, 49-59) and in WO 00/63368, described as dimers and/or trimers, actually dissociate rapidly into monomers under both reducing and non-reducing conditions, and are therefore unable to induce an antibody response.

WO 00/63368 describes a recombinant form of UK114 which differs from the natural form by a single amino acid. The absence of tags in the form claimed implies various purification steps, as described in the examples of WO 00/63368. The protein claimed is declared to be in dimeric form, but in SDS totally dissociates to a monomer, whereas under non-reducing conditions, only 90% thereof dissociates. The form described by Colombo I. et al. in Biochimica et Biophysica Acta presents 3 more amino acids (VPM) deriving from cloning at the N-terminal end, and also dissociates into a monomer. When injected into xenogeneic mammals, neither of said proteins produces a cytotoxic immune response. WO 00/63368 and Colombo et al. also state that the protein is immunologically recognised by anti-UK101 extraction antibodies, which is obvious, because the monomeric protein is almost a hapten (molecular weight 14.2 kD), which is unable to induce a good immune response apart from a weak IgG response, but is recognised by antibodies targeted against its antigenic determinants, because it binds in Western Blot to the anti-native UK114 (extraction) antibodies produced by immunising with extract UK101 which (in addition to molecule UK114, most of which dissociates into a monomer) also contains a carrier (a 50 kD glycoprotein). However, when these recombinant proteins are injected into mammals, they do not produce a cytotoxic immune response, because although they are considered to be a dimer and/or trimer, they are rapidly converted into a monomer, which is a hapten, and therefore not immunogenic alone.

DESCRIPTION OF THE INVENTION

It has now been discovered that if recombinant YjgF/YERO 57c7/UK 114 RID protein in stable polymer form is injected into xenogeneic animals, it elicits a strong, long-lasting, cytotoxic antibody response against identical and/or cross-reacting antigens expressed on malignant solid and systemic tumour cells.

The proteins according to the invention are therefore useful in the treatment, diagnosis and prevention of malignant solid and systemic tumours.

Analysis of the identity of UK114 present in various species demonstrated that identity with *Homo sapiens* (taken as 100%) ranges from 99.3% in *Macaca mulatta* to 45.6% in *Heterocephalus glaber*.

Identity values lower than 86% and higher than 60% are suitable for the purpose of the invention, as they are sufficiently xenogeneic to stimulate the antibody response but have a good identity able to produce a polyclonal antibody that recognises the determinants expressed on the tumour cell membrane. TABLE 1 shows the identity percentages of said UK 114 proteins compared with human UK114. Analysis of the identity of UK114 present in various species demonstrated that identity with *Homo sapiens* (taken as 100%) ranges from 99.3% in *Macaca mulatta* to 45.6% in *Heterocephalus glaber*.

TABLE 1

BLAST SEARCH

| Entry | Protein names | Identity |
|---|---|---|
| P52758 | Ribonuclease UK114 (*Homo sapiens*) | 100.0% |
| A0A024R9H2 | Heat-responsive protein 12, isoform CRA_a (*Homo sapiens*) | 100.0% |
| H9FNK5 | Ribonuclease UK114 (*Macaca mulatta*) | 99.3% |
| H2QWH5 | Heat-responsive protein 12 (*Pan troglodytes*) | 99.3% |
| H2PQW3 | Uncharacterised protein (*Pongo abelii*) | 99.3% |
| G7PCA5 | Ribonuclease UK114 (*Macaca fascicularis*) | 99.3% |
| G3QFT9 | Uncharacterised protein (*Gorilla gorilla gorilla*) | 99.3% |
| G1QQ41 | Uncharacterised protein (*Nomascus leucogenys*) | 99.3% |
| G7MZU3 | Ribonuclease UK114 (*Macaca mulatta*) | 97.8% |
| U3FHY9 | Ribonuclease UK114 (*Callithrix jacchus*) | 95.6% |
| G7PHN9 | Ribonuclease UK114 (*Macaca fascicularis*) | 96.3% |
| F6VKH4 | Uncharacterised protein (*Macaca mulatta*) | 94.9% |
| M3VY13 | Uncharacterised protein (*Felis catus*) | 92.0% |
| G1L170 | Uncharacterised protein (*Ailuropoda melanoleuca*) | 91.2% |
| F7A6J6 | Ribonuclease UK114-like protein (*Equus caballus*) | 92.0% |
| E2QS94 | Uncharacterised protein (*Canis familiaris*) | 92.0% |
| M3YUY4 | Uncharacterised protein (*Mustela putorius furo*) | 89.8% |
| F6VML1 | Uncharacterised protein (*Callithrix jacchus*) | 92.7% |
| G9K4S5 | Heat-responsive protein 12 (*Mustela putorius furo*) | 89.7% |
| H0WIN4 | Uncharacterised protein (*Otolemur garnettii*) | 93.3% |
| K9IWF2 | Putative ribonuclease uk114 isoform 1 (*Desmodus rotundus*) | 89.1% |
| L8I1S8 | Ribonuclease UK114 (*Bos mutus*) | 86.9% |
| Q3T114 | Ribonuclease UK114 (*Bos taurus*) | 86.1% |
| F1S0M2 | Uncharacterised protein (*Sus scrofa*) | 87.6% |
| P80601 | Ribonucase UK114 (*Capra hircus*) | 85.4% |
| P52759 | Ribonuclease UK114 (*Rattus norvegicus*) | 87.6% |
| W5P8I3 | Uncharacterised protein (*Ovis aries*) | 84.7% |
| G1Q9C4 | Uncharacterised protein (*Myotis lucifugus*) | 85.9% |
| F7B859 | Uncharacterised protein (*Monodelphis domestica*) | 88.5% |
| G3SPS4 | Uncharacterised protein (*Loxodonta africana*) | 83.2% |
| G1U8R2 | Uncharacterised protein (*Oryctolagus cuniculus*) | 82.5% |
| H3AW97 | Uncharacterised protein (*Latimeria chalumnae*) | 80.1% |
| F7H790 | Uncharacterised protein (*Macaca mulatta*) | 99.1% |
| H0YB34 | Ribonuclease UK114 (*Homo sapiens*) | 100.0% |
| F6ZTJ8 | Uncharacterised protein (*Ornithorhynchus anatinus*) | 86.7% |
| P52760 | Ribonuclease UK114 (*Mus musculus*) | 81.5% |
| G5B8Y4 | Ribonuclease UK114 (*Heterocephalus glaber*) | 80.7% |
| Q6NTT0 | MGC82310 protein (*Xenopus laevis*) | 77.2% |
| K9IFZ3 | Putative ribonuclease uk114 isoform 1 (*Desmodus rotundus*) | 81.0% |
| Q28GJ3 | Heat-responsive protein 12 (*Xenopus tropicalis*) | 77.2% |
| L8HUS2 | Uncharacterised protein (*Bos mutus*) | 80.0% |
| W5MUF4 | Uncharacterised protein (*Lepisosteus oculatus*) | 76.5% |
| Q5M8W7 | LOC496671 protein (*Xenopus tropicalis*) | 77.6% |
| H0ZP41 | Uncharacterised protein (*Taeniopygia guttata*) | 77.0% |
| U3JT39 | Uncharacterised protein (*Ficedula albicollis*) | 75.0% |
| G5E3D7 | Putative uncharacterised protein (*Hymenochirus curtipes*) | 74.4% |

TABLE 1-continued

| BLAST SEARCH | | |
|---|---|---|
| Entry | Protein names | Identity |
| W5KVI7 | Uncharacterised protein (*Astyanax mexicanus*) | 76.5% |
| I3KHW6 | Uncharacterised protein (*Oreochromis niloticus*) | 74.3% |
| E3TEU7 | Ribonuclease uk114 (*Ictalurus punctatus*) | 75.7% |
| K4G4Q6 | Heat-responsive protein 12 (*Callorhynchus milii*) | 71.5% |
| S9XJZ3 | Ribonuclease UK114 (*Camelus ferus*) | 88.9% |
| A0A098LZJ9 | Heat-responsive protein 12 (*Hypsiglena* sp. JMG-2014) | 74.3% |
| I3MHC8 | Uncharacterised protein (*Spermophilus tridecemlineatus*) | 89.7% |
| H3D6Z5 | Uncharacterised protein (*Tetraodon nigroviridis*) | 74.8% |
| Q4S2X6 | Chromosome 8 SCAF14759, whole genome shotgun sequence (*Tetraodon nigroviridis*) | 74.8% |
| G3NHG8 | Uncharacterised protein (*Gasterosteus aculeatus*) | 75.6% |
| C3KK60 | Ribonuclease UK114 (*Anoplopoma fimbria*) | 75.2% |
| E1C7E1 | Uncharacterised protein (*Gallus gallus*) | 72.7% |
| C3KJM3 | Ribonuclease UK114 (*Anoplopoma fimbria*) | 72.1% |
| H0XUH1 | Uncharacterised protein (*Otolemur garnettii*) | 81.5% |
| C3KH08 | Ribonuclease UK114 (*Anoplopoma fimbria*) | 70.6% |
| I3J3B1 | Uncharacterised protein (*Oreochromis niloticus*) | 73.7% |
| T1DKW2 | Heat-responsive protein 12 (*Crotalus horridus*) | 69.9% |
| A0A087Y9U8 | Uncharacterised protein (*Poecilia formosa*) | 70.7% |
| A0A087Y3T2 | Uncharacterised protein (*Poecilia formosa*) | 71.5% |
| Q6AXL2 | Uncharacterised protein (*Danio rerio*) | 72.1% |
| H2LCD2 | Uncharacterised protein (*Oryzias latipes*) | 72.1% |
| J3S8W6 | Heat-responsive protein 12 (*Crotalus adamanteus*) | 69.1% |
| B9EM65 | Ribonuclease UK114 (*Salmo salar*) | 70.6% |
| A0A091SB34 | Ribonuclease UK114 (*Mesitornis unicolor*) | 81.7% |
| A0A091Q1X3 | Ribonuclease UK114 (*Leptosomus discolor*) | 81.7% |
| U3J3U4 | Uncharacterised protein (*Anas platyrhynchos*) | 80.2% |
| A0A093P527 | Ribonuclease UK114 (*Pygoscelis adeliae*) | 80.0% |
| A0A091WBZ6 | Ribonuclease UK114 (*Opisthocomus hoazin*) | 80.0% |
| A0A091VG32 | Ribonuclease UK114 (*Nipponia nippon*) | 80.0% |
| A0A091J6T7 | Ribonuclease UK114 (*Egretta garzetta*) | 80.0% |
| A0A091FU34 | Ribonuclease UK114 (*Cuculus canorus*) | 80.0% |
| I3J3B0 | Uncharacterised protein (*Oreochromis niloticus*) | 70.1% |
| K4FU80 | Ribonuclease (*Callorhynchus milii*) | 67.9% |
| A0A087VAG6 | Ribonuclease UK114 (*Balearica regulorum gibberic..*) | 80.0% |
| A0A093G8Q8 | Ribonuclease UK114 (*Picoides pubescens*) | 79.8% |
| A0A093SE99 | Ribonuclease UK114 (*Manacus vitellinus*) | 78.3% |
| A0A091MX96 | Ribonuclease UK114 (*Cariama cristata*) | 80.0% |
| A0A091HE47 | Ribonuclease UK114 (*Buceros rhinoceros silvestris*) | 79.1% |
| A0A087QUR5 | Ribonuclease UK114 (*Aptenodytes forsteri*) | 79.1% |
| H0VRQ6 | Uncharacterised protein (*Cavia porcellus*) | 82.1% |
| E3TDF8 | Ribonuclease uk114 (*Ictalurus furcatus*) | 70.6% |
| A0A0A0AVW1 | Ribonuclease UK114 (*Charadrius vociferus*) | 79.1% |
| A0A091KIM5 | Ribonuclease UK114 (*Chlamydotis macqueenii*) | 78.3% |
| K4GC04 | Ribonuclease (*Callorhynchus milii*) | 67.2% |
| A0A093C3S1 | Ribonuclease UK114 (*Tauraco erythrolophus*) | 79.5% |
| G3VD69 | Uncharacterised protein (*Sarcophilus harrisii*) | 86.1% |
| A0A091EJL2 | Ribonuclease UK114 (*Corvus brachyrhynchos*) | 77.4% |
| K4GBJ3 | Ribonuclease (*Callorhynchus milii*) | 67.2% |
| A0A096MBS1 | Uncharacterised protein (*Poecilia formosa*) | 68.4% |
| A0A093HH07 | Ribonuclease UK114 (*Struthio camelus australis*) | 79.3% |
| M3ZNB1 | Uncharacterised protein (*Xiphophorus maculatus*) | 68.4% |
| A0A094NNG1 | Ribonuclease UK114 (*Podiceps cristatus*) | 77.4% |
| F7GP86 | Uncharacterised protein (*Callithrix jacchus*) | 79.7% |
| C1BLC3 | Ribonuclease UK114 (*Osmerus mordax*) | 68.6% |
| G3SJQ3 | Uncharacterised protein (*Gorilla gorilla gorilla*) | 76.9% |
| A0A091IGZ5 | Ribonuclease UK114 (*Calypte anna*) | 76.4% |
| D2GY46 | Putative uncharacterised protein (*Ailuropoda melanoleuca*) | 90.9% |
| K7E4Y7 | Uncharacterised protein (*Monodelphis domestica*) | 73.3% |
| H2UMU8 | Uncharacterised protein (*Takifugu rubripes*) | 67.7% |
| F6USW0 | Uncharacterised protein (*Canis familiaris*) | 89.9% |
| U6E0W1 | Ribonuclease UK114 (*Neovison vison*) | 89.8% |
| R0JFK7 | Ribonuclease UK114 (*Anas platyrhynchos*) | 79.2% |
| Q3B7E4 | Uncharacterised protein (*Danio rerio*) | 66.4% |
| H2TRV4 | Uncharacterised protein (*Takifugu rubripes*) | 74.6% |
| Q6DGX0 | Zgc: 92739 (*Danio rerio*) | 66.4% |
| G1TDL7 | Uncharacterised protein (*Oryctolagus cuniculus*) | 68.2% |
| C0H8I4 | Ribonuclease UK114 (*Salmo salar*) | 67.5% |
| B5XA58 | Ribonuclease UK114 (*Salmo salar*) | 67.5% |
| I3N7V1 | Uncharacterised protein (*Spermophilus tridecemlineatus*) | 69.4% |
| A0A099ZWV1 | Ribonuclease UK114 (*Tinamus guttatus*) | 81.4% |
| Q4SJ46 | Chromosome 21 SCAF14577, whole genome shotgun sequence (*Tetraodon nigroviridis*) | 58.6% |
| H0YBX3 | Ribonuclease UK114 (*Homo sapiens*) | 100.0% |
| G1KS26 | Uncharacterised protein (*Anolis carolinensis*) | 67.0% |

TABLE 1-continued

BLAST SEARCH

| Entry | Protein names | Identity |
|---|---|---|
| G3RRV5 | Uncharacterised protein (*Gorilla gorilla gorilla*) | 68.6% |
| K7G3G2 | Uncharacterised protein (*Pelodiscus sinensis*) | 70.1% |
| S4R576 | Uncharacterised protein (*Petromyzon marinus*) | 63.2% |
| G3UJF8 | Uncharacterised protein (*Loxodonta africana*) | 71.7% |
| A0A093HP53 | Ribonuclease UK114 (*Gavia stellata*) | 79.8% |
| G3VGS7 | Uncharacterised protein (*Sarcophilus harrisii*) | 58.5% |
| B9EQ43 | Ribonuclease UK114 (*Salmo salar*) | 62.4% |
| M3ZJS5 | Uncharacterised protein (*Xiphophorus maculatus*) | 72.4% |
| A0A091SVV5 | Ribonuclease UK114 (*Nestor notabilis*) | 63.2% |
| V8P2W9 | Ribonuclease (*Ophiophagus hannah*) | 50.7% |
| F6VVM7 | Uncharacterised protein (*Ornithorhynchus anatinus*) | 77.9% |
| A0A060YX21 | Oncorhynchus mykiss genomic scaffold, scaffold_20632 (*Oncorhynchus mykiss*) | 71.9% |
| G5AL28 | Ribonuclease UK114 (*Heterocephalus glaber*) | 45.6% |
| G1NHU5 | Uncharacterised protein (*Meleagris gallopavo*) | 73.2% |
| H2UH67 | Uncharacterised protein (*Takifugu rubripes*) | 34.2% |
| V9L685 | ATP-binding domain 4 (*Callorhynchus milii*) | 30.0% |
| W5N319 | Uncharacterised protein (*Lepisosteus oculatus*) | 27.9% |
| W5N314 | Uncharacterised protein (*Lepisosteus oculatus*) | 27.9% |
| U3JT08 | Uncharacterised protein (*Ficedula albicollis*) | 34.5% |
| V9KG05 | ATP-binding domain-containing protein 4 (*Callorhynchus milii*) | 30.0% |
| G3P8F9 | Uncharacterised protein (*Gasterosteus aculeatus*) | 30.3% |
| W5L5R2 | Uncharacterised protein (*Astyanax mexicanus*) | 26.0% |
| F1P550 | Uncharacterised protein (*Gallus gallus*) | 36.8% |
| A0A096LQQ1 | Uncharacterised protein (*Poecilia formosa*) | 29.4% |
| P83145 | Ribonuclease UK114 (*Gallus gallus*) | 53.7% |
| R4G926 | Uncharacterised protein (*Anolis carolinensis*) | 26.6% |
| I3IYS6 | Uncharacterised protein (*Oreochromis niloticus*) | 25.4% |
| Q6GPL5 | MGC83562 protein (*Xenopus laevis*) | 47.3% |
| A0A087YAW6 | Uncharacterised protein (*Poecilia formosa*) | 26.2% |
| F6XPS3 | Uncharacterised protein (*Xenopus tropicalis*) | 47.3% |
| M4A570 | Uncharacterised protein (*Xiphophorus maculatus*) | 26.7% |
| E5RIP8 | Ribonuclease UK114 (*Homo sapiens*) | 100.0% |
| H3BDI6 | Uncharacterised protein (*Latimeria chalumnae*) | 25.7% |
| E7F9Q1 | Diphthine--ammonia ligase (*Danio rerio*) | 25.0% |
| A0A060ZCJ4 | Oncorhynchus mykiss genomic scaffold, scaffold_38082 (*Oncorhynchus mykiss*) | 24.4% |
| R0KDP7 | Uncharacterised protein (*Anas platyrhynchos*) | 40.5% |
| G1NI69 | Uncharacterised protein (*Meleagris gallopavo*) | 24.0% |
| F7FWD1 | Uncharacterised protein (*Monodelphis domestica*) | 22.4% |

The stable polymeric recombinant YjgF/YER057c/UK 114 RID proteins according to the invention (hereinafter called PRP14) comprise three or more monomer units each having a sequence of 137 amino acids, and therefore have a molecular weight of about 42.6 or more.

A preferred sequence of the monomer unit is the sequence SEQ ID 1:

GSHMSSLVRRIISTAKAPAAIGPYSQAVLVDRTIYISGQLGMDPASGQLV
PGGVVEEAKQALTNIGEILKAAGCDFTNVVKATVLLADINDFSAVNDVYK
QYFQSSFPARAAYQVAALPKGGRVEIEAIAVQGPLTTASL.

Said sequence, shown here as an example, deriving from *Capra hircus* and expressed by suitable vectors in *Escherichia coli* as described below, is characterised by four more amino acids at the N-terminal end than the above-mentioned sequences. Said additional amino acids are G-S-H-M (glycine-serine-histidine-methionine). It has been found that due to the presence of said four additional amino acids at the N-terminal end, the polymeric forms consisting of clusters of more than one 14.2 kDA monomer unit are more stable than the dimeric or trimeric form of the native or recombinant YjgF/YERO 57c7/UK 114 proteins previously described. In fact, while the known proteins, in aqueous solution, give rise to unstable dimeric or trimeric forms that dissociate rapidly into the monomer, the sequence SEQ ID 1 gives rise to polymeric (dimeric and trimeric) forms which do not dissociate, thus maintaining their immunogenic capacity.

In fact, only a stable polymeric form leads to a 3D conformation responsible for the RID functional activity proper of the proteins of the YjgF/YER057c/UK114 family (Lambrecht J A et al., J. Biol. Chem. 2012, 287, 3454-3461; Mistiniene E et al., Bioconjugate Chem. 2003, 14, 1243-1252; Dhawan L et al., Mol. Cell. Biol., 2012, 32, 3768-3775; Flynn J M et al., Mol. Microbiol., 2013, 89(4)751-759; Ernst D C et al., J. Bacteriology, 2014, 196 (18), 3335-3342; Niehaus T D et al., BMC Genomics, 2015, 16, 382).

According to a preferred aspect of the invention, the protein, which is xenogeneic for humans, is expressed in *Escherichia coli* cells transformed with an expression vector that expresses the protein with a polyhistidine segment at the N-terminal end, allowing efficient purification with a single chromatography stage on nickel resin.

Figure 1:
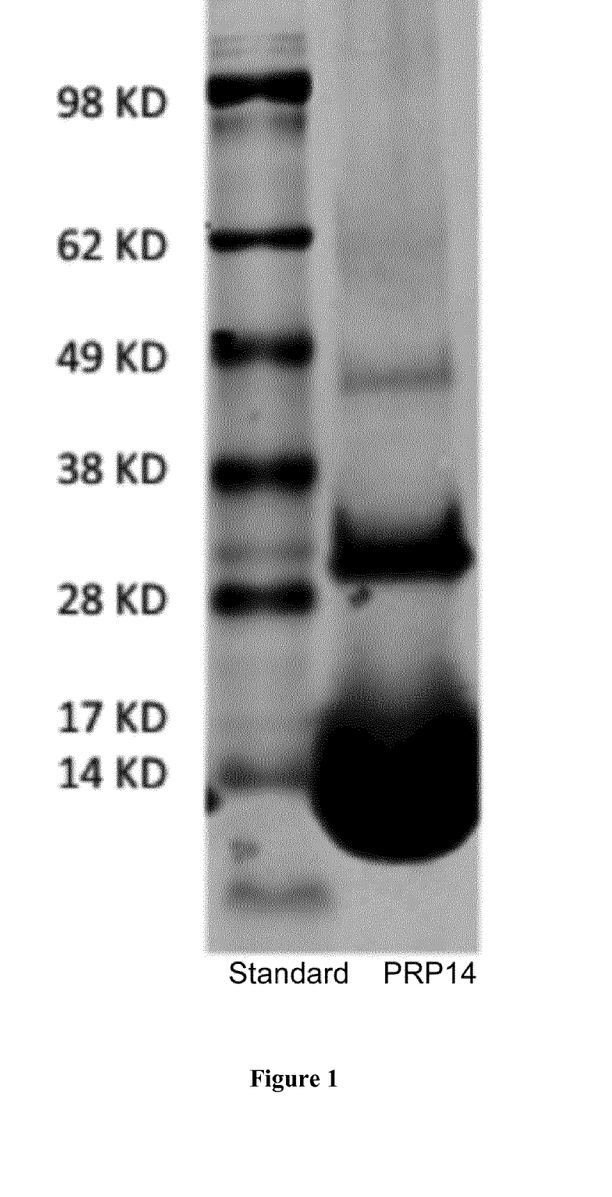
FIG. 1 shows protein bands in western blotting corresponding to polymeric, dimeric and trimeric forms of the 14.2 kDa monomer.

The resulting protein presents bands in WB corresponding to polymeric, dimeric and trimeric forms of the 14.2 kDa monomer unit (FIG. 1).

Figure 2A:
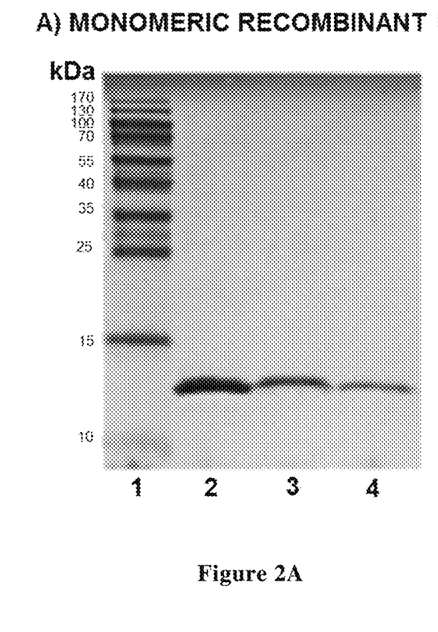
FIG. 2A shows the monomeric form of protein UK 114 expressed in yeast in wester blotting obtained by blotting with rabbit antibody RIC1 immunized with protein PRP14.

The trimeric form of the PRP14 protein according to the invention constitutes the correct physiological structure of the protein empowered with RID function, as well as with antigenic and cytotoxic activity. It can dissociate, but only partly, into dimeric and monomeric form, unlike the UK 114 proteins described in WO 0063368 and Colombo et al. and protein UK 114 expressed in yeast, which dissociate totally in monomeric form, as can be seen from Western Blotting, obtained by blotting with rabbit antibody RIC1, immunised with said protein PRP14, shown in FIG. 2/A, wherein track 1 refers to the standard of molecular weights; track 2 refers to recombinant protein UK 114 described in Colombo I. et al.; track 3 refers to recombinant protein UK 114 expressed in yeast, and track 4 refers to the recombinant protein described in WO 00/63368.

The sequences of said proteins are reported in Table 2 below.

TABLE 2

Recombinant UK114 of the invention (SEQ ID 1)

GSHMSSLVRRIISTAKAPAAIGPYSQAVLVDRTIYISGQLGMDPASGQLV
PGGVVEEAKQALTNIGEILKAAGCDFTNVVKATVLLADINDFSAVNDVYK
QYFQSSFPARAAYQVAALPKGGRVEIEAIAVQGPLTTASL

Recombinant UK1144 from *E. coli* (Colombo I. et al., Biochim. Biophys. Acta, 1998, 1442, 49-59) (SEQ ID 6)

VPMSSLVRRIISTAKAPAAIGPYSQAVLVDRTIYISGQLGMDPASGQLVP
GGVVEEAKQALTNIGEILKAAGCDFTNVVKATVLLADINDFSAVNDVYKQ
YFQSSFPARAAYQVAALPKGGRVEIEAIAVQGPLTTASL

Recombinant UK114 from yeast (SEQ ID 7)

MSSLVRRIISTAKAPAAIGPYSQAVLVDRTIYISGQLGMD
PASGQLVPGGVVEEAKQALTNIGEILKAAGCDFTNVVKATVLLADINDFS
AVNDVYKQYFQSSFPARAAYQVAALPKGGR VEIEAIAVQGPLTTASL

Recombinant UK114 from *E. coli* (WO 0063368) (SEQ ID 8)

VPMSSLVRRIISTAKAPAAIGPYSQAVLVDRTIYISGQLGMD
PASGQLVPGGVVEEAKQALTNIGEILKAAGCDFTNVVKATVLLADINDFS
AVNDVYKQYFQSSFPARAAYQVAALPKGGRVEIEAIAVQGPLTTASV

Figure 2B:
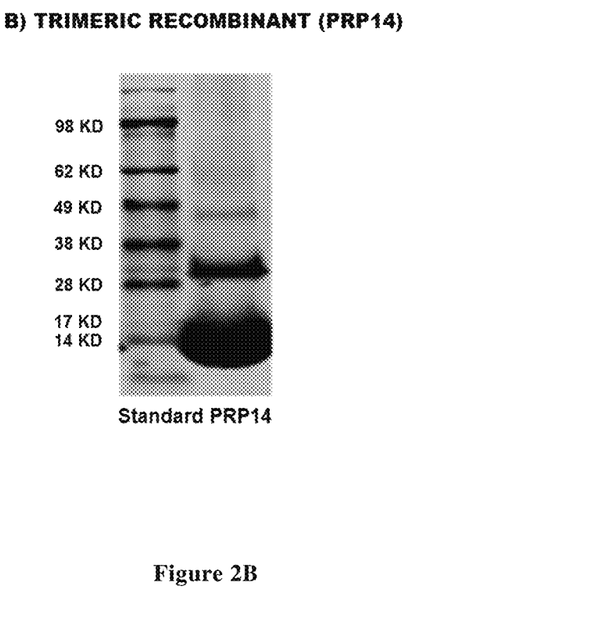
FIG. 2B shows the comparison with stable polymer PRP14.

FIG. 2/b shows the comparison with stable polymer PRP14. It has been demonstrated that 90% of the protein described in WO 00/63368, produced by recombinant techniques, dissociates to a monomer even under non-reducing conditions.

It has also been found that further polymer forms PRP14 can be obtained by treating the proteins described above with strong acids such as perchloric acid. Perchloric acid also has an oxidising action, and the formation of polymers of sequence SEQ ID1 can also be obtained by using an oxidant such as hydrogen peroxide.

It has also been observed that the formation of polymers of sequence SEQ ID1 can be obtained by using crosslinking agents such as glutaraldehyde.

Figure 3:
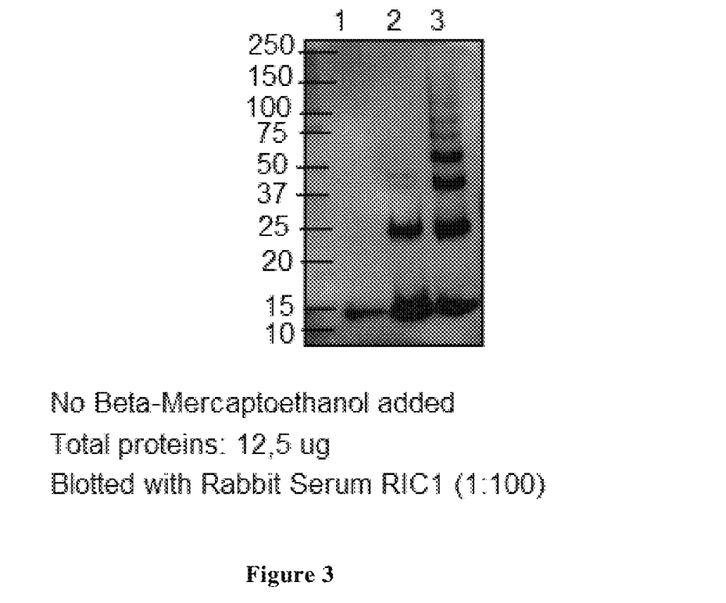
FIG. 3 shows western blotting of the recombinant protein described in WO0063368, protein PRP14 and the polymer forms obtained after treatment with perchloric acid.

Under said conditions, the proteins cluster, giving rise to the formation of the forms according to the invention, which have high molecular weights and are therefore more immunogenic (FIG. 3: track 1: dissociated protein, track 2: trimeric PRP 14, track 3: protein PRP14 treated with HC104).

Said trimeric and polymeric forms express IgM-competent antigenic determinants. Moreover, acid treatment of the proteins allows the identification and/or modification of antigenic determinants that further enhance the antigen capacity, especially in terms of the IgM response, which is mainly responsible for cytotoxicity, but without inducing modifications in the primary structure or destroying the quaternary structure of the protein.

Figure 4:
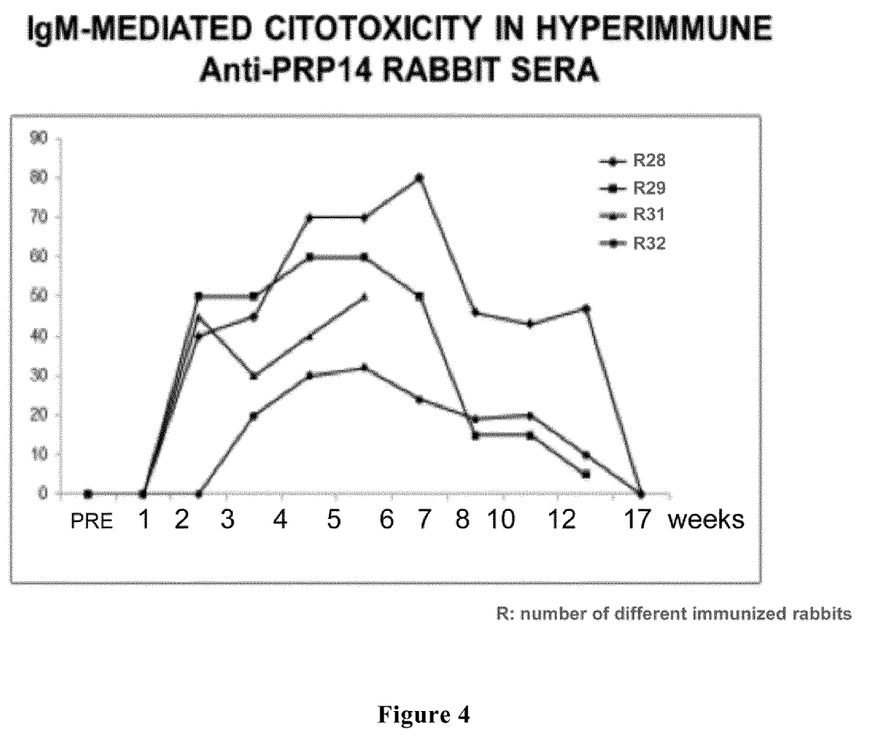
FIG. 4 shows IgM-mediated cytotoxicity in hyperimmune anti-PRP14 Rabbit Sera.

The IgMs thus obtained are cytotoxic towards tumour cells, and their presence in hyperimmune sera persists for much longer than the normal IgM response to common antigens. Said polymers produce a marked increase in the immunological capacity of the protein, and therefore a corresponding increase in the immune response, which has very marked cytotoxic, not cytostatic characteristics (as in the case of native UK114, most of which is reduced to monomeric form, as demonstrated by mass analysis), due not only to the class G immunoglobulins, but mainly to the class M immunoglobulins which, contrary to current immunological theory, remain in circulation for months (FIG. 4).

Unlike UK101 and native UK 114, the proteins according to the invention induce an antibody response without the aid of adjuvants or carriers which, however, can be used to further strengthen the immune response.

The polymeric recombinant proteins according to the invention, preferably administered parenterally, in particular subcutaneously or intramuscularly, are particularly useful for the treatment of malignant tumours, preventive immunisation against recurrence in patients previously treated for tumours, adjuvant treatment, and vaccination of individuals at risk of onset or recurrence of said tumours in general.

For the recommended therapeutic or preventive uses the protein will be administered subcutaneously or intramuscularly in the form of solutions or suspensions in sterile aqueous carriers, optionally conjugated with adjuvants to further strengthen the immune response.

The protein in polymer form can also be administered by other routes, such as sublingually or topically. The doses for therapeutic, prophylactic and vaccinal applications can range from 5 to 40 mg per administration. A typical vaccination protocol involves 4 administrations, one every fortnight. 20/30 days after the last dose, a booster dose 4 times higher is given. Immunotherapy is monitored with laboratory tests to evaluate the antibody titre and cytotoxicity. The treatment can continue until a satisfactory clinical result is achieved (reduction or disappearance of the tumour mass), with boosters given at intervals, depending on the antibody titre monitored with the laboratory tests, to prevent a fall in the antibody titre or overimmunisation, leading to the risk of immune tolerance.

The polymeric recombinant protein can also be used to prepare monoclonal antibodies (anti-PRP14 Mabs) which are useful for intramuscular or intravenous passive immunotherapy, and passive seroprophylaxis of immunodepressed patients and/or those who fail to respond to specific immunotherapy.

For example, human monoclonal antibodies can be obtained by fusing a human-mouse myeloma K6H6/B5 with lymphocytes transformed with Epstein-Barr virus from patients pre-treated with the protein. Unlike the common practice for passive immunotherapy, which uses IgG monoclonal antibodies, it is preferable to use IgM-secreting clones which, in the presence of complement, are cytotoxic to tumour cells. Alternatively, a mixture of both types of monoclonal antibody (IgG and IgM) can be used.

Humanised murine IgM monoclonal antibodies or human IgM-secreting monoclonal antibodies produced in transgenic animals can also be used.

Immunocytochemistry has demonstrated that human tumours exhibit over 80% positivity to polymeric hyperimmune anti-protein sera (83%) and to polymeric anti-protein Mabs (93%), as shown in Table 3 below.

TABLE 3

IMMUNOCYTOLOGICAL LOCALISATION IN CANCER TISSUES

| Tumour | Anti PRP14+/− | Mab Anti PRP14+/− |
|---|---|---|
| Breast | 12/0 | 3/0 |
| Stomach | 12/9 | 9/0 |
| Colon/rectum | 21/0 | 15/0 |
| Lung | 3/3 | 1/1 |
| Bladder | 6/0 | 3/0 |
| Prostate | 9/0 | 4/2 |
| Corpus uteri | 3/0 | 3/0 |
| Gall bladder | 3/0 | 3/0 |
| NOS | 6/3 | 3/0 |
| TOTAL | 75/15 | 44/3 |

The positivity is far more evident in percentage terms in adenocarcinomas (neoplasms of glandular origin which constitute 65% of malignant human tumours), and is not equally present in all cells of the same tumour. Some tumours, such as breast, pancreas, kidney, liver and prostate tumours, are therefore intensely positive, while others alternate intensely positive with negative or low-positivity areas (lung, colon) due to the presence of mucinous cells which do not express the antigen on their membrane.

In systemic tumours, leukaemias, lymphomas, myelomas and sarcomas, the positivity is 60%. The invention is described in detail in the examples set out below.

Example 1: Preparation of Recombinant Protein UK 114 from *E. coli* in Stably Trimeric Form: PRP14

Expression vector pET-15b is used for the expression of recombinant protein UK114 from *Escherichia coli*. To transfer the nucleotide sequence encoding UK114 from a plasmid preceding the vector pET-15b, the sequence of UK114 is amplified by PCR, using the following pair of primers:

UK-Nde-FOR (SEQ ID 2):
5' AGCATATTCGACTGA-CATATGTCGTCTTTGGTCAGAAGGAT-3' UK-Xho-REV (SEQ ID 3):
5' ATCGTCGGGCTCACTCGAGCTAGAGT-GATGCTGTCGTGAGA-3' The product of PCR is digested with restriction enzymes NdeI and XhoI, and the resulting fragment is eluted from the gel.

The resulting fragment of DNA encoding UK114 is cloned in the vector which expresses the protein sequence fused to a polyhistidine tag and to a cleavage site recognised by a specific protease positioned at the N-terminal end.

The plasmid created, called pET15b-UK114, is used to transform *Escherichia coli* cells (DH5).

The transformers were screened. The cloned nucleotide sequence of plasmid pET15b-UK114 proved to be correctly fused to the vector and error-free.

Nucleotide sequence SEQ ID 4 (the start codon of UK114 is underlined and bolded):

ATGGGCAGCAGCCATCATCATCATCATCACAGCAGCGGCCTGGTGCCG

CGCGGCAGCCATATGTCGTCTTTGGTCAGAAGGATAATCAGCACGGCGAA

AGCCCCCGCGGCCATTGGTCCCTACAGTCAGGCTGTGTTAGTCGACAGGA

CCATTTACATTTCAGGACAGCTAGGTATGGACCCTGCAAGTGGACAGCTT

GTGCCAGGAGGGGTGGTAGAAGAGGCTAAACAGGCTCTTACAAACATAGG

TGAAATTCTGAAAGCAGCAGGCTGTGACTTCACGAATGTGGTAAAAGCAA

CGGTTTTGCTGGCTGACATAAATGACTTCAGTGCTGTCAATGATGTCTAC

AAACAATATTTCCAGAGTAGTTTTCCGGCGAGAGCTGCTTACCAGGTTGC

TGCTTTGCCCAAAGGAGGCCGTGTTGAGATCGAAGCAATAGCTGTGCAAG

GACCTCTCACGACAGCATCACTCTAA

The amino-acid sequence SEQ ID 5 of the fusion protein His-tag-UK114 is shown below (the segment containing His-tag up to the thrombin cleavage site is underlined and bolded):

<u>MGSSHHHHHHSSGLVPR</u>GSHMSSLVRRIISTAKAPAAIGPYSQAVLVDRT

IYISGQLGMDPASGQLVPGGVVEEAKQALTNIGEILKAAGCDFTNVVKAT

VLLADINDFSAVNDVYKQYFQSSFPARAAYQVAALPKGGRVEIEAIAVQG

PLTTASL

The amino-acid sequence after thrombin treatment is shown below (SEQ ID 1):

GSHMSSLVRRIISTAKAPAAIGPYSQAVLVDRTIYISGQLGMDPASGQLV
PGGVVEEAKQALTNIGEILKAAGCDFTNVVKATVLLADINDFSAVNDVYK
QYFQSSFPARAAYQVAALPKGGRVEIEAIAVQGPLTTASL.

To express protein UK114, the plasmid is transferred from strain DH5a to the expression strain (Rosetta DE3).

The transformed cells are grown in a suitable medium (LB+antibiotics), and expression of the protein is induced with IPTG for 4 hours at 37° C. This induction time and the temperature of 37° C. are ideal for the stable trimeric protein UK114 (PRP14).

Electrophoresis on polyacrylamide gel containing SDS (SDS-PAGE), and staining of the protein with Coomassie Blue, is conducted to verify the expression of the protein.

UK114-His is analysed by Western Blotting using the primary anti-poly-His antibody.

The clones tested express the recombinant protein UK114 at a high level. The protein is present in the soluble fraction of the cell extract.

The protein can be purified by exploiting the affinity of the polyhistidine tag for nickel resin. The soluble fraction obtained from cells collected 4 hours after induction at 37° C. is incubated with the resin to allow the Histag of the recombinant protein to bind to the nickel conjugated with the resin. The flow-through (everything not bonded to the resin) is then collected, and after various washes the protein is eluted with a high concentration of imidazole which competes with histidine for the nickel bond.

The sample, obtained by pooling the eluates with a significant protein concentration, is dialysed in 50 mM $NaH_2PO_4$, 300 mM NaCl, pH 7.5.

The sample is then incubated with thrombin, a serine protease which specifically recognises the cleavage site at the N-terminal end between the protein sequence and the Histag sequence, allowing the tag to be removed.

A portion of the digested sample is used to conduct analytical gel filtration with a SUPERDEX 75 column; by exploiting the known molecular weight standards, the molecular weight of recombinant protein UK114 can be obtained (MW=42.6 KDa). The purified protein, if compared with the molecular weight of the monomer, is a stable trimer, indicated by the code PRP14.

As demonstrated by Western Blot analysis (FIG. 1), under these reducing conditions the protein does not dissociate, but remains stably monomeric, dimeric and trimeric. The protein therefore presents good immunogenic activity.

Example 2: Manufacture of Polymers by Treating the Dimeric Recombinant Protein with 2M Perchloric Acid, Hydrogen Peroxide and Glutaraldehyde A) Treatment with 2M Perchloric Acid 5 ml of a protein solution obtained according to example 1 (3 mg/ml) is mixed at 4° C. with 5 ml of 2 M perchloric acid. Sodium acetate is added to adjust the pH to 4.1, and the resulting solution is incubated overnight at 4° C. Any precipitates are removed by centrifugation at 10,000 rpm for 1 hour.

The solution is dialysed under stirring at 4° C. against PBS, using a dialysis tube with a cut-off of 1000 Da, and filtered through an 0.2 micron filter. Under these conditions, as demonstrated by Western Blotting (FIG. 3) performed with a rabbit antibody obtained by immunisation with the trimeric protein of example 1, different polymers of the same protein are formed, with covalent (and therefore not dissociable) bonds, with the same antigenic determinants, and having higher molecular weights up to about 70 kD. In FIG. 3, track 1 refers to the recombinant protein described in WO0063368; track 2 refers to protein PRP14 of example 1, and track 3 refers to the polymer forms obtained after treatment with perchloric acid.

B) Treatment with Hydrogen Peroxide 5 ml of a protein solution obtained according to example 1 (3 mg/ml) is mixed at room temperature with 5 ml of 30% hydrogen peroxide. The resulting solution is incubated for 2 hours at room temperature.

The solution is dialysed under stirring at 4° C. against PBS, using a dialysis tube with a cut-off of 1000 Da, and filtered through an 0.2 micron filter. Under said conditions, different polymers of the same protein are formed, with covalent bonds, which therefore cannot be dissociated. The resulting polymers have a molecular weight corresponding to those obtained using perchloric acid.

C) Treatment with Glutaraldehyde 5 ml of a protein solution obtained according to example 1 (3 mg/ml) is mixed at 4° C. with 1 ml of an 0.01 M solution of glutaraldehyde in phosphate buffer pH 7.2, 0.1 M. The resulting solution is incubated overnight at 4° C. Any precipitates are removed by centrifugation at 10,000 rpm for 1 hour.

The solution is dialysed under stirring at 4° C. against PBS, using a dialysis tube with a cut-off of 1000 Da, and filtered through an 0.2 micron filter. Under said conditions, different polymers of the same protein are formed, with covalent bonds, which therefore cannot be dissociated, with the same antigenic determinants, and having higher molecular weights up to about 70 kD. The resulting polymers have a molecular weight corresponding to those obtained using perchloric acid or hydrogen peroxide.

Example 3: In Vitro Binding of Anti-Protein PRP14 Antibodies to Tumour Cells

The binding to antigens present on the cell membrane and complement-mediated cytotoxic activity on numerous human tumour cell lines (KATO 3°, HT29, TSA, MCF7, JURKAT), and the absence of cytotoxicity on non-tumoral cell lines (NCTC, MCF10, HUVEC), was demonstrated using hyperimmune anti-PRP14 sera produced in mammals and the corresponding Mabs.

A) FACS Analysis Using Human Tumour Cells HT29 as Target.

Cells not fixed and not permeabilised were tested with rabbit RIC1 antibody obtained by immunising with the protein of example 1 (PRP14)

Figure 5:
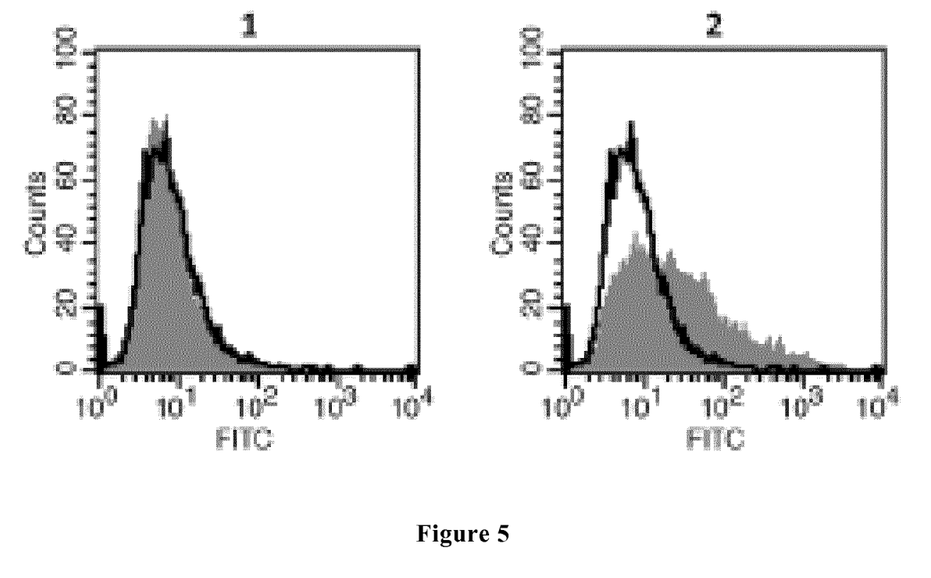
FIG. 5 shows flow cytometry analysis of anti-protein serum of example 1 compared to control serum.
Figure 6:
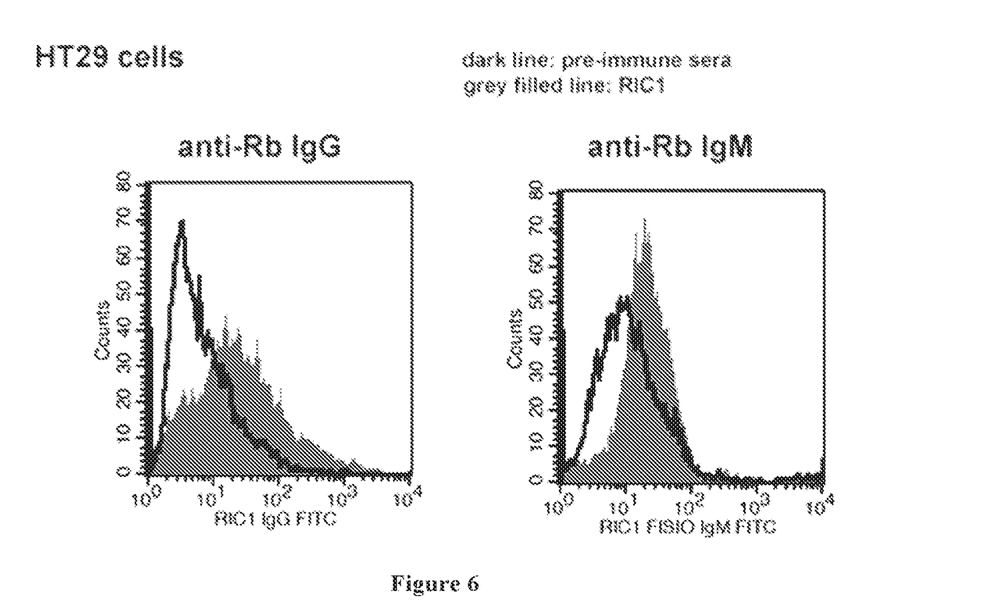
FIG. 6 show flow cytometry analysis of the bond of IgG and IgM antibodies present in the rabbit serum immunized with the trimeric protein of example 1 compared to control serum.

Flow cytometry analysis (FACS) demonstrates the antibody bond with the antigen present on the cell membrane (FIG. 5): 1 control serum; 2 anti-protein serum of example 1, and the bond of the IgG and IgM antibodies present in the rabbit serum immunised with the trimeric protein of example 1 (PRP14, FIG. 6).

IgM antibodies are mainly responsible for the cytotoxic effect.

B) ELISA Assay, Using HT29 Cells Adhering to the Incubation Well as Target. Cells Dried and Fixed but not Permeabilised.

Figure 7:
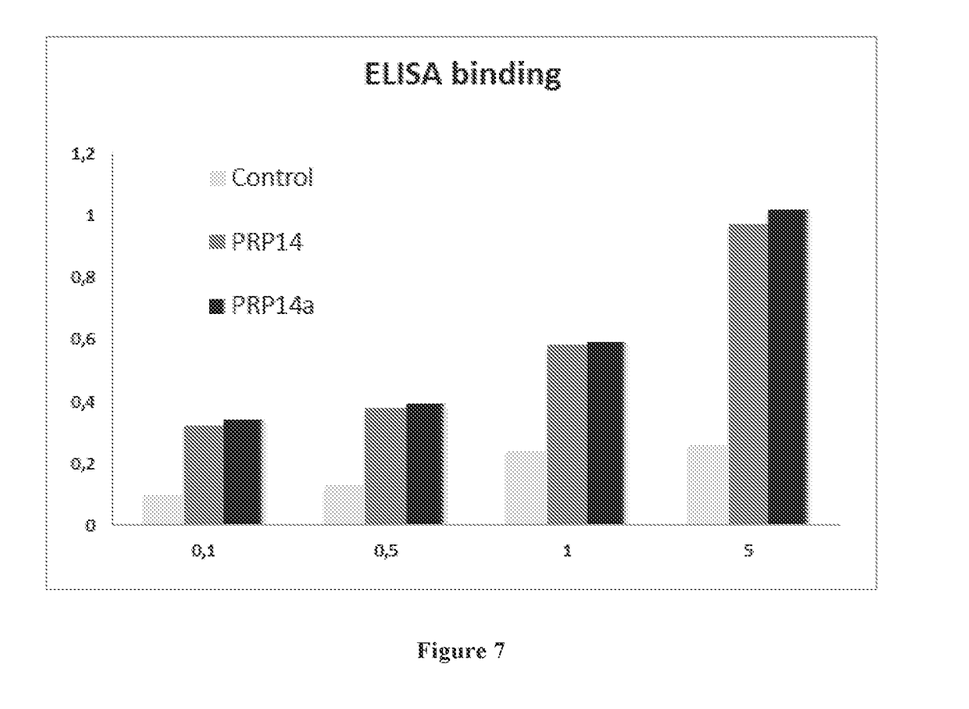
FIG. 7 shows the results of the test performed with different concentration of antisera.

FIG. 7 shows the results of the test performed with different concentrations (0.1 to 5%) of the various antisera obtained: rabbit antibody obtained by immunising with the protein of example 1 (PRP14); rabbit antibody obtained by immunising with the polymeric protein obtained by treating with perchloric acid (PRP a). Control: pre-immune rabbit serum.

C) Cytotoxic Activity Test, Using the MTT Assay. HT29 Cells Tested with Rabbit Antisera Immunised with Polymeric Proteins UK114+Complement.

Figure 8:
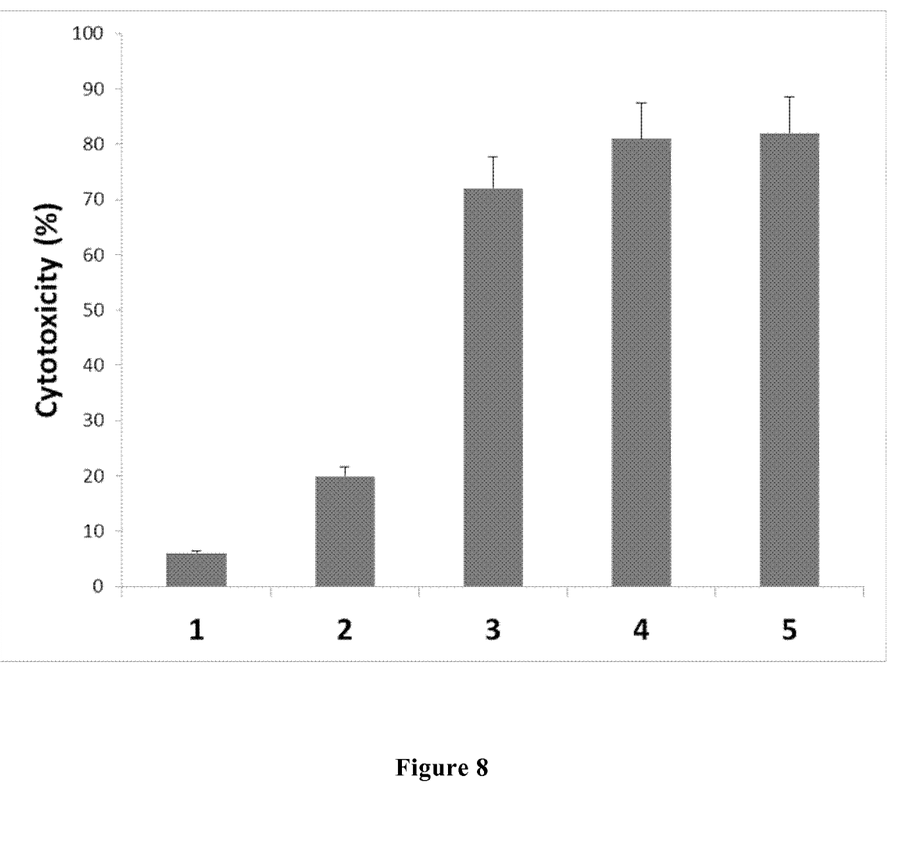
FIG. 8 shows cytotoxicity activity test on HT29 cells tested with rabbit antisera immunized with polymeric proteins UK114 + complement.
Figure 9A:
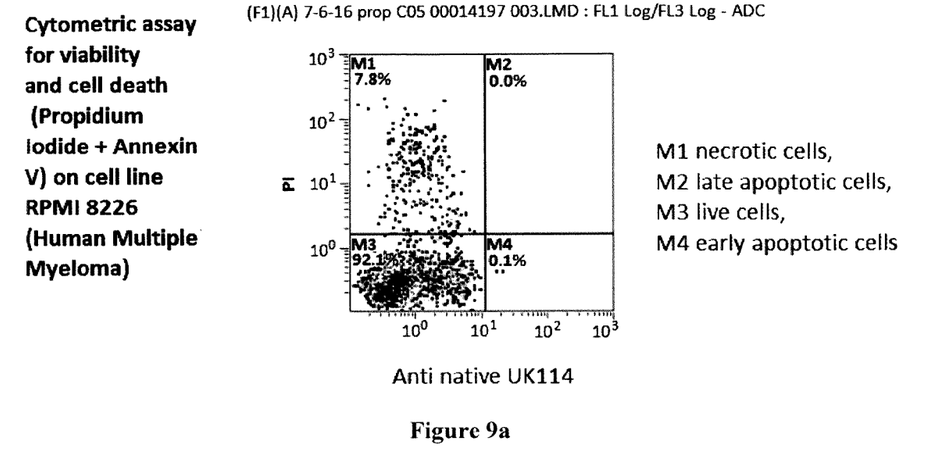
FIG. 9a, FIG. 9b, FIG. 9C and FIG. 9D show cytometry assay for viability and cell death on cell line RPMI 8226 labelled with UK101, UK114, negative control and anti-PRP14, respectively.
Figure 9B:
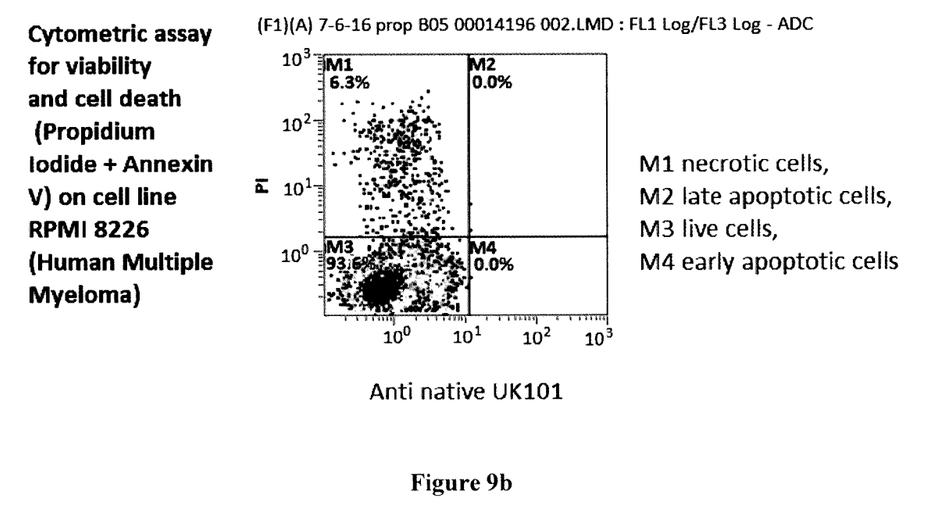
Figure 9C:
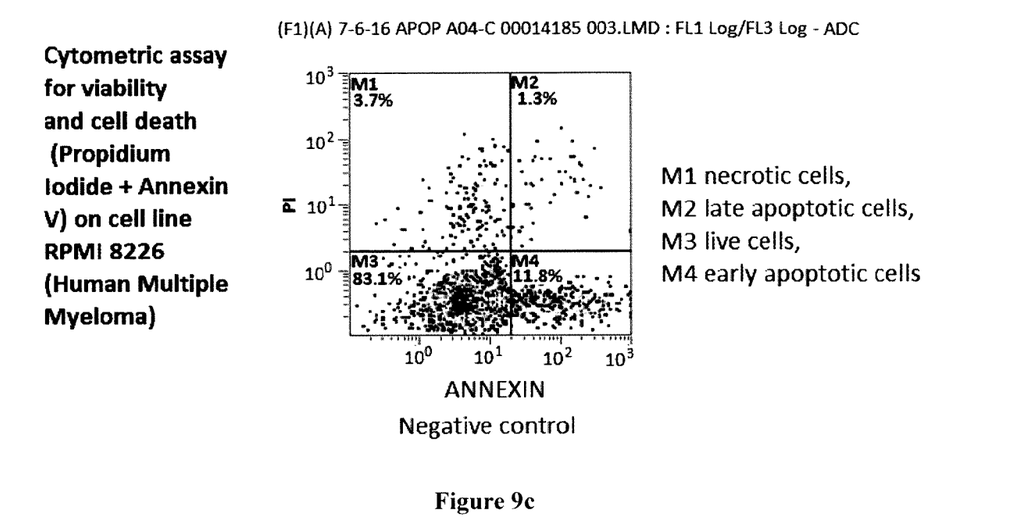
Figure 9D:
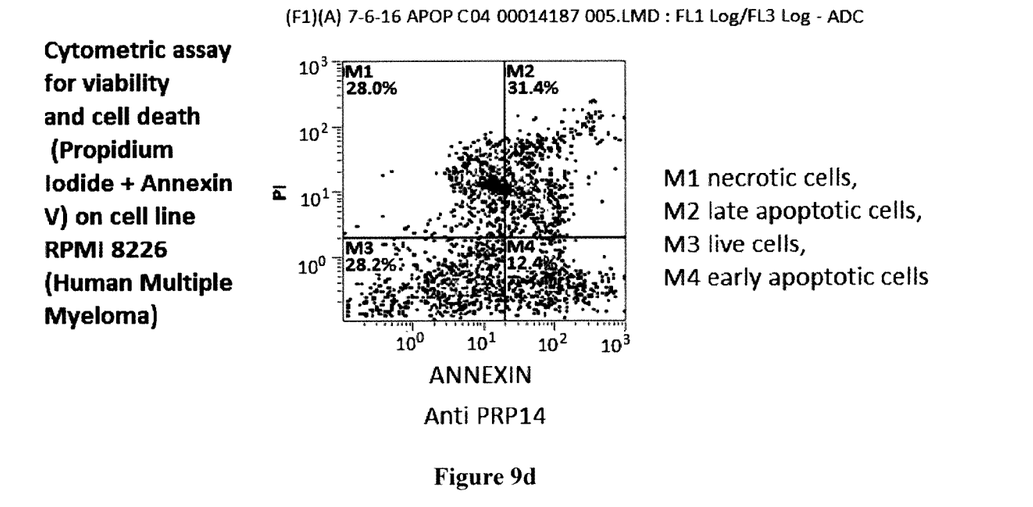

The cytotoxicity tests are reported in FIG. 8: 1) Control: pre-immune rabbit serum; 2) anti-native UK 114 mAb (International Journal of Oncology 8: 543-548, 1996); 3) rabbit antibody obtained by immunising with polymeric protein PRP14; 4) rabbit antibody obtained by immunising with polymeric protein PRP14 treated with perchloric acid; 5) rabbit antibody obtained by immunising with polymeric protein PRP14 treated with $H_2O_2$.

Example 4: Cytotoxicity vs. Cytostaticity

ATP lite is a cell viability measurement test that does not distinguish between cytotoxic and cytostatic effects.

Using the Annexin V plus Propidium Iodide test, it was found that for anti-PRP14, of the 78% viability loss of the neoplastic cells detected with the ATP lite tests, 60% was due to a cytotoxic effect (apoptosis) and 60% to a cytostatic effect, while for native antibodies against UK101/UK114, almost the entire loss of viability was due to a cytostatic, not a cytotoxic effect (FIG. 9).

Example 5: Treatment with PRP14 of Balb/c) Mice Carrying Murine Colon Adenocarcinoma (C26)

C26 is a highly aggressive murine tumour which grows rapidly, reaching dimensions incompatible with the life of Balb/c mice (weight 18/20 grams) in 20 days.

Figure 10:
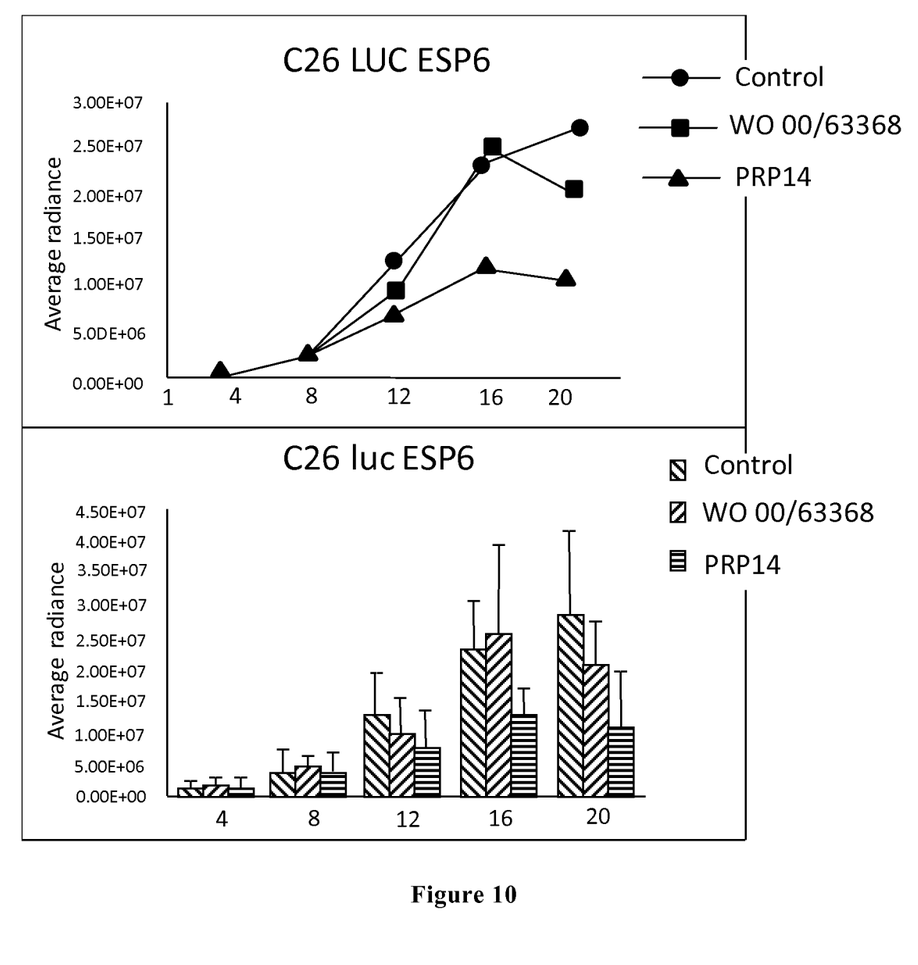
FIG. 10 shows reduction of tumor growth in BALB/c mice treated with polymeric protein PRP14 compared to control mice and mice treated with recombinant protein UK114 describe in WO 00/63368.

4 days after tumour implantation (when the neoplastic mass is already appreciable), the treated mice received 10 micrograms of polymeric protein PRP14 on the 4th, 11th and 18th days, while the control animals received saline solution or the recombinant protein UK114 described in WO 00/63368. The test was conducted with the luciferase technique. As demonstrated in FIG. 10, treatment of BALB/c mice with polymeric protein PRP14 gave rise to a significant (>50%) reduction in the growth and tumour mass of C26 carcinomas implanted subcutaneously. There was no significant reduction in the control animals or the mice treated with the recombinant protein UK114 described in WO 00/63368.

Example 6): Inhibition of Mammary Carcinogenesis in BALB/c Mice Carrying the Activated HER2 Rat Gene This is an experimental model, extensively illustrated in the literature (Calogero et al., Breast Cancer Research 2007, 9:21), wherein mammary carcinomas appear in female BALB/c mice that overexpress the HER2 neu gene. The onset of the carcinomas, which appear at well-established fixed times, can be monitored over time with this model.

20 animals were used, and the appearance of mammary carcinomas was monitored over time. The model is based on the finding that in these animals, atypical hyperplasia develops spontaneously in the mammary ducts and lobules in the 2nd week of life. In the 10th week the epithelial cells occlude and distend the ducts, which take on the appearance of carcinomas in situ. As the weeks pass, said pre-neoplastic lesions are transformed into invasive carcinomas. By the end of the experiment, in the 33rd week, palpable invasive carcinomas had appeared in all 10 mammary glands.

To evaluate the efficacy of preventive immunisation with protein PRP14 in preventing or slowing the appearance of invasive carcinomas, the polymeric protein+Freund's adjuvant was administered to 10 animals (test animals) from the 8th week of life. A subcutaneous booster was then administered every 4 weeks. An equal number of animals (controls) were treated with saline solution.

The difference between the incidence and tumour appearance curves and the number of multiple tumours that appeared was evaluated in the test and control animals.

A significant reduction in said parameters was observed between the test and control animals. Only 10% of the animals treated with PRP14 presented tumour implants, and the size and number of said implants were smaller.

The result therefore confirms the ability of antitumoral vaccination with the polymeric protein to inhibit and/or prevent carcinomatous transformation and the formation of invasive carcinomas induced in mammary epithelial cells by the mitogenic activity of the activated HER2 gene.

Example 7: Passive Seroprophylaxis in Nude Mice Carrying Human Tumour HT29

HT29 human colon adenocarcinoma cells were implanted into nude mice to demonstrate the transmission of antitumoral immunity to the nude mouse carrying human tumours, using hyperimmune mammalian sera (immunised with protein PRP14) and sera from the same mammals before immunisation with said protein.

It was demonstrated that the hyperimmune serum of mammals immunised with protein PRP14 considerably reduces implantation of human tumours in the nude mouse. Only 20% of tumours took root in the animals that underwent seroprophylaxis (with hyperimmune mammalian serum), with a considerable increase in implantation latency and survival, compared with 100% of the controls injected with pre-immune control serum.

In the treated animals the growth time of the tumours, which were implanted in any event, was three times less than that of the controls, and the survival rate was at least twice as high as in the controls (TABLE 4).

TABLE 4

HT-29 cells in nude mice. Treatment with trimeric anti-protein and anti-PRP14 sera. Control with pre-immune serum.

| Serum | No. of Tumours | Latency (D) | Survival (D) |
|---|---|---|---|
| Pre-immune | 12/12 | 9 | 30 |
| Anti-PRP14 | 3/12 | 28 | 87 |

---

The invention claimed is:

1. Method of treating adenocarcinomas or tumor responsive to a recombinant polymeric protein in subjects in need thereof, wherein said polymeric proteins comprises two to fifteen monomeric units and wherein the protein monomeric unit has SEQ ID NO: 1, said method comprising:

administering said recombinant protein to said subjects.

2. The method according to claim 1, wherein said protein is expressed by *Escherichia coli*.

3. The method according to claim 1, wherein said polymeric protein is obtained by treating the protein monomeric unit of SEQ ID NO:1 with acids, oxidizing or cross-linking agents.

4. The method according to claim 1, further comprising passive immunization with monoclonal antibodies of subjects affected with or treated for adenocarcinomas or tumor responsive to said recombinant polymeric protein, adjuvant therapy, or treatment of subjects at risk of novel or recurrent malignant adenocarcinoma or tumors responsive to said recombinant polymeric protein.

* * * * *

SEQUENCE LISTING

```
<160> NUMBER OF SEQ ID NOS: 8

<210> SEQ ID NO 1
<211> LENGTH: 140
<212> TYPE: PRT
<213> ORGANISM: Capra hircus

<400> SEQUENCE: 1

Gly Ser His Met Ser Ser Leu Val Arg Arg Ile Ile Ser Thr Ala Lys
1               5                   10                  15

Ala Pro Ala Ala Ile Gly Pro Tyr Ser Gln Ala Val Leu Val Asp Arg
            20                  25                  30

Thr Ile Tyr Ile Ser Gly Gln Leu Gly Met Asp Pro Ala Ser Gly Gln
        35                  40                  45

Leu Val Pro Gly Gly Val Val Glu Glu Ala Lys Gln Ala Leu Thr Asn
    50                  55                  60

Ile Gly Glu Ile Leu Lys Ala Ala Gly Cys Asp Phe Thr Asn Val Val
65                  70                  75                  80

Lys Ala Thr Val Leu Leu Ala Asp Ile Asn Asp Phe Ser Ala Val Asn
                85                  90                  95

Asp Val Tyr Lys Gln Tyr Phe Gln Ser Ser Phe Pro Ala Arg Ala Ala
            100                 105                 110

Tyr Gln Val Ala Ala Leu Pro Lys Gly Gly Arg Val Glu Ile Glu Ala
```

```
             115                 120                 125
Ile Ala Val Gln Gly Pro Leu Thr Thr Ala Ser Leu
    130                 135                 140

<210> SEQ ID NO 2
<211> LENGTH: 41
<212> TYPE: DNA
<213> ORGANISM: Artificial Sequence
<220> FEATURE:
<223> OTHER INFORMATION: synthetic primer

<400> SEQUENCE: 2
agcatattcg actgacatat gtcgtctttg gtcagaagga t              41

<210> SEQ ID NO 3
<211> LENGTH: 41
<212> TYPE: DNA
<213> ORGANISM: Artificial Sequence
<220> FEATURE:
<223> OTHER INFORMATION: Synthetic primer

<400> SEQUENCE: 3
atcgtcgggc tcactcgagc tagagtgatg ctgtcgtgag a              41

<210> SEQ ID NO 4
<211> LENGTH: 474
<212> TYPE: DNA
<213> ORGANISM: Artificial Sequence
<220> FEATURE:
<223> OTHER INFORMATION: expression vector

<400> SEQUENCE: 4
atgggcagca gccatcatca tcatcatcac agcagcggcc tggtgccgcg cggcagccat      60
atgtcgtctt tggtcagaag gataatcagc acggcgaaag ccccgcggc cattggtccc      120 tacagtcagg ctgtgttagt cgacaggacc atttacattt caggacagct aggtatggac     180
cctgcaagtg gacagcttgt gccaggaggg gtggtagaag aggctaaaca ggctcttaca     240
aacataggtg aaattctgaa agcagcaggc tgtgacttca cgaatgtggt aaaagcaacg     300
gttttgctgg ctgacataaa tgacttcagt gctgtcaatg atgtctacaa acaatatttc     360
cagagtagtt ttccggcgag agctgcttac caggttgctg ctttgcccaa aggaggccgt     420
gttgagatcg aagcaatagc tgtgcaagga cctctcacga cagcatcact ctaa           474

<210> SEQ ID NO 5
<211> LENGTH: 157
<212> TYPE: PRT
<213> ORGANISM: Artificial Sequence
<220> FEATURE:
<223> OTHER INFORMATION: His-tag-fusion protein

<400> SEQUENCE: 5

Met Gly Ser Ser His His His His His His Ser Ser Gly Leu Val Pro
1               5                  10                  15

Arg Gly Ser His Met Ser Ser Leu Val Arg Arg Ile Ile Ser Thr Ala
            20                  25                  30

Lys Ala Pro Ala Ala Ile Gly Pro Tyr Ser Gln Ala Val Leu Val Asp
        35                  40                  45

Arg Thr Ile Tyr Ile Ser Gly Gln Leu Gly Met Asp Pro Ala Ser Gly
    50                  55                  60

Gln Leu Val Pro Gly Gly Val Val Glu Glu Ala Lys Gln Ala Leu Thr
65                  70                  75                  80
```

```
Asn Ile Gly Glu Ile Leu Lys Ala Ala Gly Cys Asp Phe Thr Asn Val
                85                  90                  95

Val Lys Ala Thr Val Leu Leu Ala Asp Ile Asn Asp Phe Ser Ala Val
            100                 105                 110

Asn Asp Val Tyr Lys Gln Tyr Phe Gln Ser Ser Phe Pro Ala Arg Ala
        115                 120                 125

Ala Tyr Gln Val Ala Ala Leu Pro Lys Gly Gly Arg Val Glu Ile Glu
    130                 135                 140

Ala Ile Ala Val Gln Gly Pro Leu Thr Thr Ala Ser Leu
145                 150                 155

<210> SEQ ID NO 6
<211> LENGTH: 139
<212> TYPE: PRT
<213> ORGANISM: Capra hircus

<400> SEQUENCE: 6

Val Pro Met Ser Ser Leu Val Arg Arg Ile Ile Ser Thr Ala Lys Ala
1               5                   10                  15

Pro Ala Ala Ile Gly Pro Tyr Ser Gln Ala Val Leu Val Asp Arg Thr
            20                  25                  30

Ile Tyr Ile Ser Gly Gln Leu Gly Met Asp Pro Ala Ser Gly Gln Leu
        35                  40                  45

Val Pro Gly Gly Val Val Glu Glu Ala Lys Gln Ala Leu Thr Asn Ile
    50                  55                  60

Gly Glu Ile Leu Lys Ala Ala Gly Cys Asp Phe Thr Asn Val Val Lys
65                  70                  75                  80

Ala Thr Val Leu Leu Ala Asp Ile Asn Asp Phe Ser Ala Val Asn Asp
                85                  90                  95

Val Tyr Lys Gln Tyr Phe Gln Ser Ser Phe Pro Ala Arg Ala Ala Tyr
            100                 105                 110

Gln Val Ala Ala Leu Pro Lys Gly Gly Arg Val Glu Ile Glu Ala Ile
        115                 120                 125

Ala Val Gln Gly Pro Leu Thr Thr Ala Ser Leu
    130                 135

<210> SEQ ID NO 7
<211> LENGTH: 137
<212> TYPE: PRT
<213> ORGANISM: Capra hircus

<400> SEQUENCE: 7

Met Ser Ser Leu Val Arg Arg Ile Ile Ser Thr Ala Lys Ala Pro Ala
1               5                   10                  15

Ala Ile Gly Pro Tyr Ser Gln Ala Val Leu Val Asp Arg Thr Ile Tyr
            20                  25                  30

Ile Ser Gly Gln Leu Gly Met Asp Pro Ala Ser Gly Gln Leu Val Pro
        35                  40                  45

Gly Gly Val Val Glu Glu Ala Lys Gln Ala Leu Thr Asn Ile Gly Glu
    50                  55                  60

Ile Leu Lys Ala Ala Gly Cys Asp Phe Thr Asn Val Lys Ala Thr
65                  70                  75                  80

Val Leu Leu Ala Asp Ile Asn Asp Phe Ser Ala Val Asn Asp Val Tyr
                85                  90                  95

Lys Gln Tyr Phe Gln Ser Ser Phe Pro Ala Arg Ala Ala Tyr Gln Val
            100                 105                 110
```

```
Ala Ala Leu Pro Lys Gly Gly Arg Val Glu Ile Glu Ala Ile Ala Val
        115                 120                 125

Gln Gly Pro Leu Thr Thr Ala Ser Leu
    130                 135

<210> SEQ ID NO 8
<211> LENGTH: 139
<212> TYPE: PRT
<213> ORGANISM: Capra hircus

<400> SEQUENCE: 8

Val Pro Met Ser Ser Leu Val Arg Arg Ile Ile Ser Thr Ala Lys Ala
1               5                   10                  15

Pro Ala Ala Ile Gly Pro Tyr Ser Gln Ala Val Leu Val Asp Arg Thr
            20                  25                  30

Ile Tyr Ile Ser Gly Gln Leu Gly Met Asp Pro Ala Ser Gly Gln Leu
        35                  40                  45

Val Pro Gly Gly Val Val Glu Glu Ala Lys Gln Ala Leu Thr Asn Ile
    50                  55                  60

Gly Glu Ile Leu Lys Ala Ala Gly Cys Asp Phe Thr Asn Val Val Lys
65                  70                  75                  80

Ala Thr Val Leu Leu Ala Asp Ile Asn Asp Phe Ser Ala Val Asn Asp
                85                  90                  95

Val Tyr Lys Gln Tyr Phe Gln Ser Ser Phe Pro Ala Arg Ala Ala Tyr
            100                 105                 110

Gln Val Ala Ala Leu Pro Lys Gly Gly Arg Val Glu Ile Glu Ala Ile
        115                 120                 125

Ala Val Gln Gly Pro Leu Thr Thr Ala Ser Val
    130                 135
```

UNITED STATES PATENT AND TRADEMARK OFFICE
CERTIFICATE OF CORRECTION

| | |
|---|---|
| PATENT NO. | : 11,352,398 B2 |
| APPLICATION NO. | : 16/468921 |
| DATED | : June 7, 2022 |
| INVENTOR(S) | : Alberto Bartorelli Cusani |

It is certified that error appears in the above-identified patent and that said Letters Patent is hereby corrected as shown below:

On the Title Page

Item (54) and in the Specification, Column 1, Lines 1-5, -- RECOMBINANT PROTEIN UK 114 IN STABLE POLYMER FORM FOR USE IN THE TREATMENT, DIAGNOSIS AND PREVENTION OF MALIGNANT SOLID AND SYSTEMIC TUMOURS -- should read -- "NOVEL RECOMBINANT PROTEIN UK 114 IN STABLE POLYMER FORM FOR USE IN THE TREATMENT, DIAGNOSIS AND PREVENTION OF MALIGNANT SOLID AND SYSTEMIC TUMOURS" --

Signed and Sealed this
Seventeenth Day of January, 2023

Katherine Kelly Vidal
*Director of the United States Patent and Trademark Office*